(12) United States Patent
Roberts et al.

(10) Patent No.: US 9,973,736 B2
(45) Date of Patent: May 15, 2018

(54) MOBILE WORKSTATION HAVING NAVIGATION CAMERA

(71) Applicant: TOUCHPOINT MEDICAL, INC., Concordville, PA (US)

(72) Inventors: Carey Roberts, Wilkes-Barre, PA (US); Jeffrey C. Olson, Wilkes-Barre, PA (US); Robert Sobie, Wilkes-Barre, PA (US)

(73) Assignee: TOUCHPOINT MEDICAL, INC., Concordville, PA (US)

( * ) Notice: Subject to any disclaimer, the term of this patent is extended or adjusted under 35 U.S.C. 154(b) by 313 days.

(21) Appl. No.: 14/768,616

(22) PCT Filed: Feb. 19, 2014

(86) PCT No.: PCT/US2014/017122
§ 371 (c)(1),
(2) Date: Aug. 18, 2015

(87) PCT Pub. No.: WO2014/130532
PCT Pub. Date: Aug. 28, 2014

(65) Prior Publication Data
US 2016/0006992 A1  Jan. 7, 2016

Related U.S. Application Data

(60) Provisional application No. 61/766,375, filed on Feb. 19, 2013.

(51) Int. Cl.
*H04N 7/00* (2011.01)
*H04N 7/18* (2006.01)
(Continued)

(52) U.S. Cl.
CPC ............. *H04N 7/185* (2013.01); *A61B 50/10* (2016.02); *A61B 50/13* (2016.02); *G01C 21/00* (2013.01);
(Continued)

(58) Field of Classification Search
USPC ......................................................... 348/113
See application file for complete search history.

(56) References Cited

U.S. PATENT DOCUMENTS 9,158,975 B2 * 10/2015 Lipton ............... G06K 9/00771
2004/0085456 A1    5/2004 Kwag et al.
(Continued)

FOREIGN PATENT DOCUMENTS

WO        2007002941        1/2007

OTHER PUBLICATIONS

Supplementary European Search Report dated Sep. 23, 2016 for European Application No. 14754272.4, 3 pages.
(Continued)

*Primary Examiner* — Chikaodili E Anyikire
(74) *Attorney, Agent, or Firm* — RatnerPrestia

(57) ABSTRACT

A mobile computer workstation includes a base assembly including a plurality of wheels, an adjustable column assembly mounted to the base assembly and adapted to support a computer monitor, and a camera configured to communicate a video signal, the camera being mounted on the workstation such that a line of sight of the camera is directed rearward from the computer monitor. The workstation further includes a computing device stored within the workstation operatively coupled to the camera and the computer monitor. The computing device is configured to determine whether the workstation is moving based on a comparison of a sensed motion of the workstation and a predetermined motion threshold and, in response to the comparison, initiate the
(Continued)

camera, receive the video signal from the camera, and display the video signal on the computer monitor.

20 Claims, 5 Drawing Sheets

(51) Int. Cl.
    *G01C 21/20*     (2006.01)
    *G01C 21/00*     (2006.01)
    *H04N 5/225*     (2006.01)
    *H04N 5/232*     (2006.01)
    *A61B 50/13*     (2016.01)
    *A61B 50/10*     (2016.01)
    *A61B 17/00*     (2006.01)

(52) U.S. Cl.
    CPC ......... *G01C 21/206* (2013.01); *H04N 5/2253* (2013.01); *H04N 5/232* (2013.01); *A61B 2017/00199* (2013.01)

(56) References Cited

U.S. PATENT DOCUMENTS

| | | | |
|---|---|---|---|
| 2004/0186357 A1* | 9/2004 | Soderberg | A61B 5/00 600/300 |
| 2009/0174536 A1 | 7/2009 | Rao | |
| 2009/0322492 A1* | 12/2009 | Hannah | A47F 10/04 340/10.5 |
| 2010/0324380 A1* | 12/2010 | Perkins | A61B 5/0002 600/301 |
| 2011/0279958 A1* | 11/2011 | Clark | A61B 5/0002 361/679.02 |
| 2012/0093294 A1 | 4/2012 | Lalena et al. | |
| 2014/0177924 A1* | 6/2014 | Argue | G06K 9/00771 382/104 |

OTHER PUBLICATIONS

Extended European Search Report dated Sep. 7, 2016 for European Application No. 14754272.4, 6 pages.
International Search Report and Written Opinion of the ISA, ISA/US, dated Jun. 3, 2014.

* cited by examiner

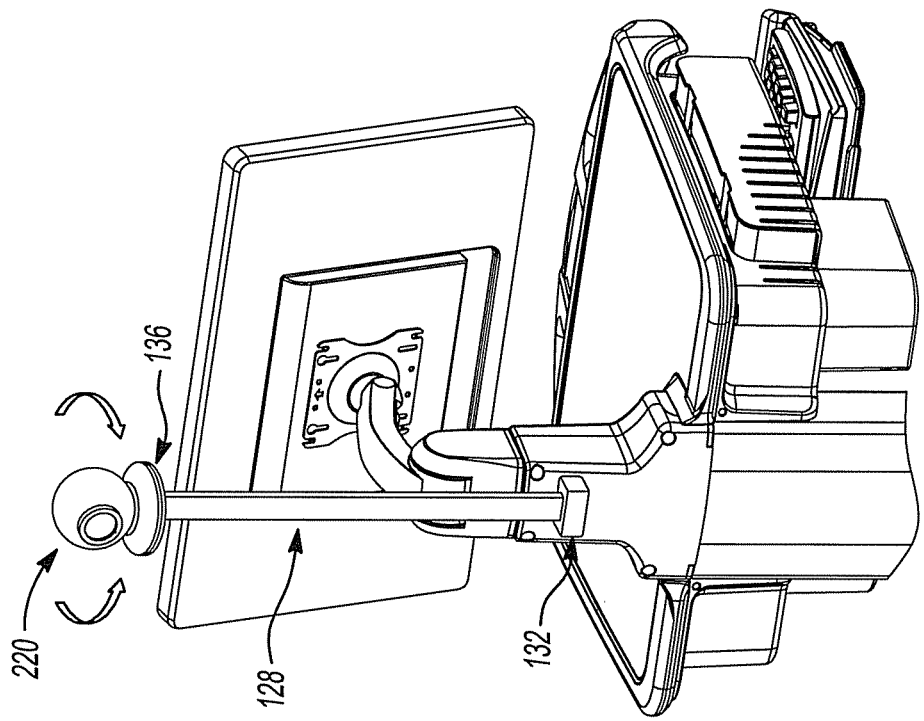
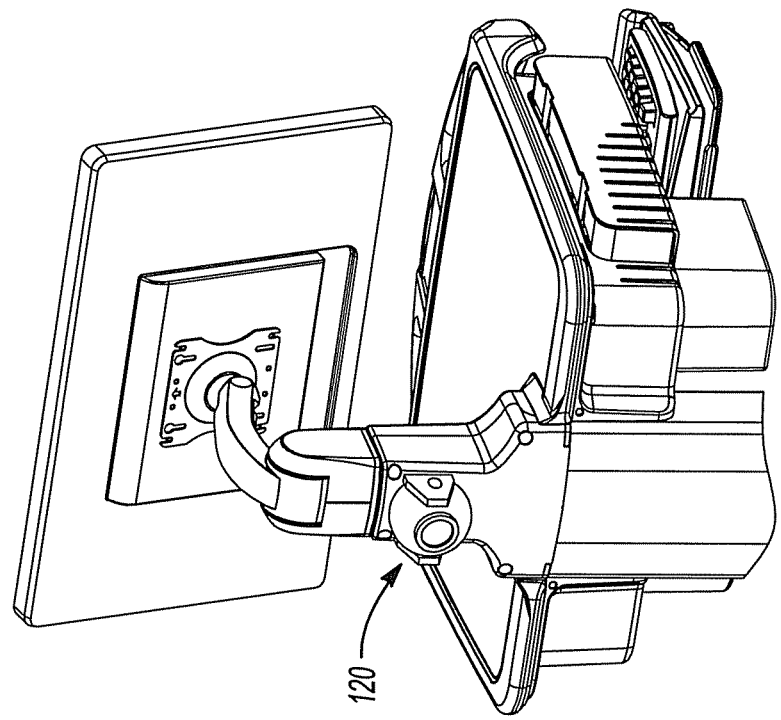

MOBILE WORKSTATION HAVING NAVIGATION CAMERA

CROSS-REFERENCE TO RELATED APPLICATIONS

This application is a 371 National Phase of International Application PCT/US2014/017122, filed on Feb. 19, 2014 and published in English as WO 2014/130532 A1 on Aug. 28, 2014, which claims the benefit of U.S. Provisional Application No. 61/766,375, filed on Feb. 19, 2013. The entire disclosure of the above application is incorporated herein by reference.

FIELD

The present disclosure relates to a mobile workstation and, more particularly, to a point of application workstation of the type that can include a computer, a display, a keyboard tray or drawer, a work surface, optional storage, and a rechargeable power supply, and a navigation camera for improved maneuverability.

BACKGROUND

The statements in this section merely provide background information related to the present disclosure and may not constitute prior art.

One type of point-of-application workstation known in the art is a point-of-care ("POC") workstation, which may be specifically adapted for use in a medical facility, such as a hospital. A POC workstation intended for healthcare applications is used primarily by nurses, doctors, clinicians or other healthcare practitioners for tracking and modifying electronic medical records, displaying various medical diagnostic imaging, telemedicine, delivering medications, and implementing Barcode Medication Administration protocols. Typically, the workstation includes an integrated computer, a display or monitor that is located above a height-adjustable work surface, and an input device tray. The work surface can typically be adjusted up and down to allow the user to use the workstation while sitting or standing.

POC workstations provide a mobile work platform and empower healthcare professionals to move about their workspace accompanied by a computer and work platform as they perform their various work-related tasks. Because the workstations are mobile, they can be rolled from room-to-room, location-to-location throughout the workspace. While navigating the workstation from one location to another, however, the workstation's display has the potential to partially obstruct or limit the workstation user's field of vision. Consequently, users often manipulate the workstation to accommodate its transport. Instead of pushing the workstation directly from a working position, they often maneuver the workstation to a "sideways" orientation or alter the ergonomic settings of the workstation before transporting it (such as lowering the work surface or adjusting the monitor to an desirable position), or pull the workstation from behind, for example. Maneuvering the workstation in these ways, however, is not preferred.

SUMMARY

In accordance with the teachings of the present disclosure, a point of application workstation is disclosed as including a camera that aids a user in the navigation of the workstation from location-to-location and enables the user to maneuver the workstation in a more preferred orientation.

Point-of-application workstations are utilized in a variety of commercial settings that can include applications in a healthcare environment, such as diagnostic applications and pharmaceutical dispensing applications. Other commercial settings include inventory control applications, maintenance applications, food service applications, quality control applications, shipping and receiving applications, manufacturing assembly/parts tracking applications, or portable point-of-sale location applications.

The workstation generally can include base, a power unit, a support structure, a work surface, an optional storage unit, a monitor assembly, a control, and a navigation camera.

The base unit provides a foundation for the workstation and houses a power unit for the workstation. The base unit may include a dolly assembly having wheels mounted beneath its bottom surface, such as swiveling casters, for example. The dolly assembly enables the workstation to be mobile and easily moved by rolling.

The workstation also includes a power unit for providing electrical power to the workstation and its accessories and/or peripheral components. The power unit is typically housed in the base unit. The power unit may comprise a charging system and one or more rechargeable batteries. The charging system receives AC power from, for example, a wall outlet, and delivers DC power to the batteries to charge them.

A navigation camera is mounted to the workstation in a rearward-facing manner such that its field of view is directed behind the workstation. The navigation camera can be mounted to the monitor assembly. Alternatively, the navigation camera can be mounted to a camera mount. The camera can be mounted to the workstation such that it is positionable between a forward-facing direction where it can serve as the camera in a video conferencing system and a rearward facing direction where it can serve as a navigation aid. The rearward-facing camera can be activated when the user is moving and/or maneuvering the workstation from location-to-location and the camera's image can be displayed on the monitor. Consequently, the user is able to see, via the displayed image, what is behind the workstation. In such a manner, the monitor, which may otherwise partially obstruct or inhibit the user's view, is rendered "invisible" to the user such that the user can "see through" the monitor. As a result, the user is provided with greater visibility while maneuvering the workstation in its intended manner.

The navigation camera enables a user to see behind the workstation so the user is able to properly maneuver the workstation from location-to-location with confidence and avoid having to look around the monitor, push the workstation in a less then optimal position or re-orient the monitor an each time the workstation is relocated.

Further areas of applicability will become apparent from the description provided herein. It should be understood that the description and specific examples are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 5 is rear perspective view of an exemplary mobile computing workstation incorporating a camera according to the teachings of the present disclosure; and FIG. 6 is rear perspective view of an alternative exemplary mobile computing workstation incorporating a camera according to the teachings of the present disclosure.

DETAILED DESCRIPTION

Figure 1:
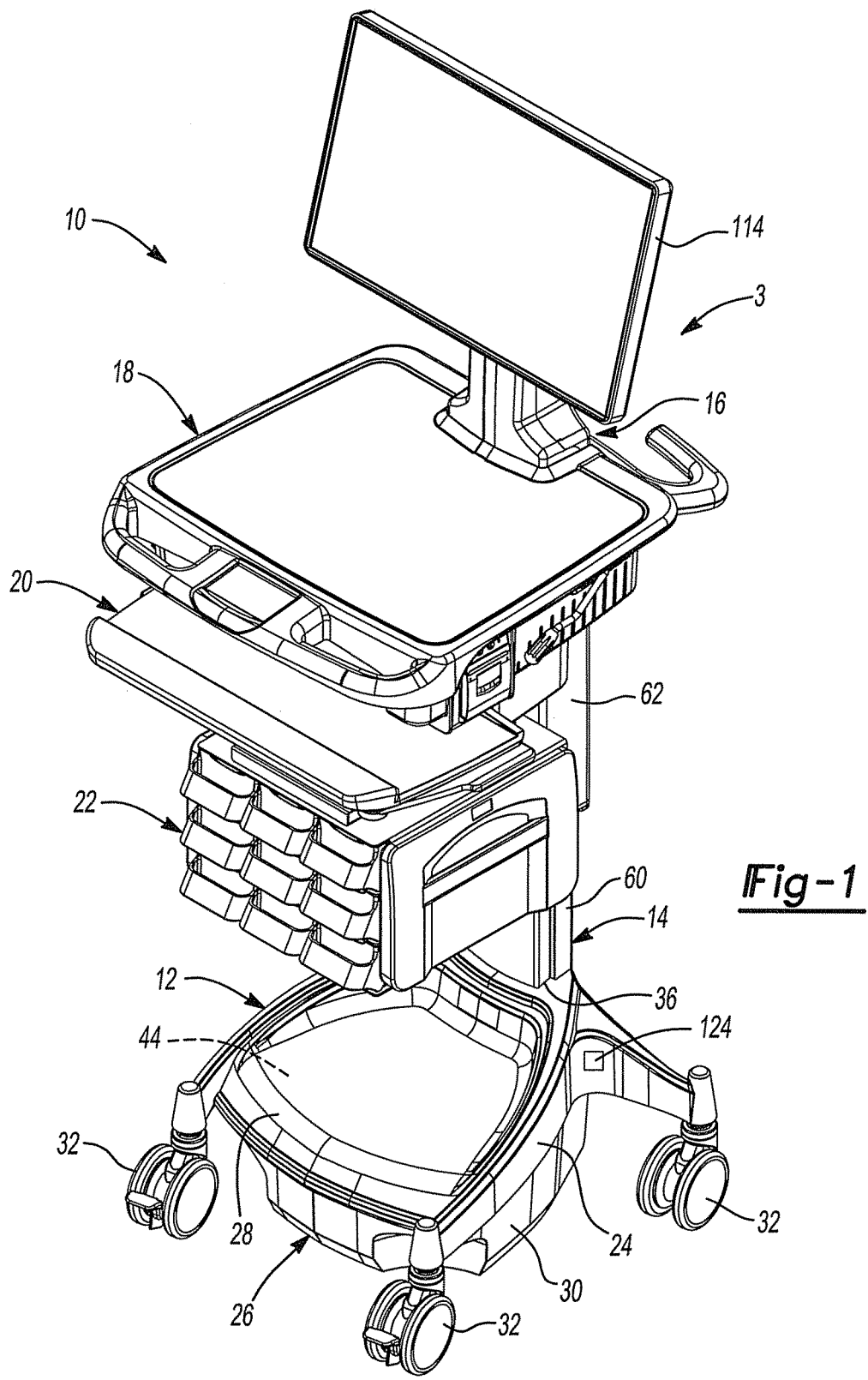
FIG. 1 is a perspective view of an exemplary mobile computer workstation according to the principles of the present disclosure.
Figure 2:
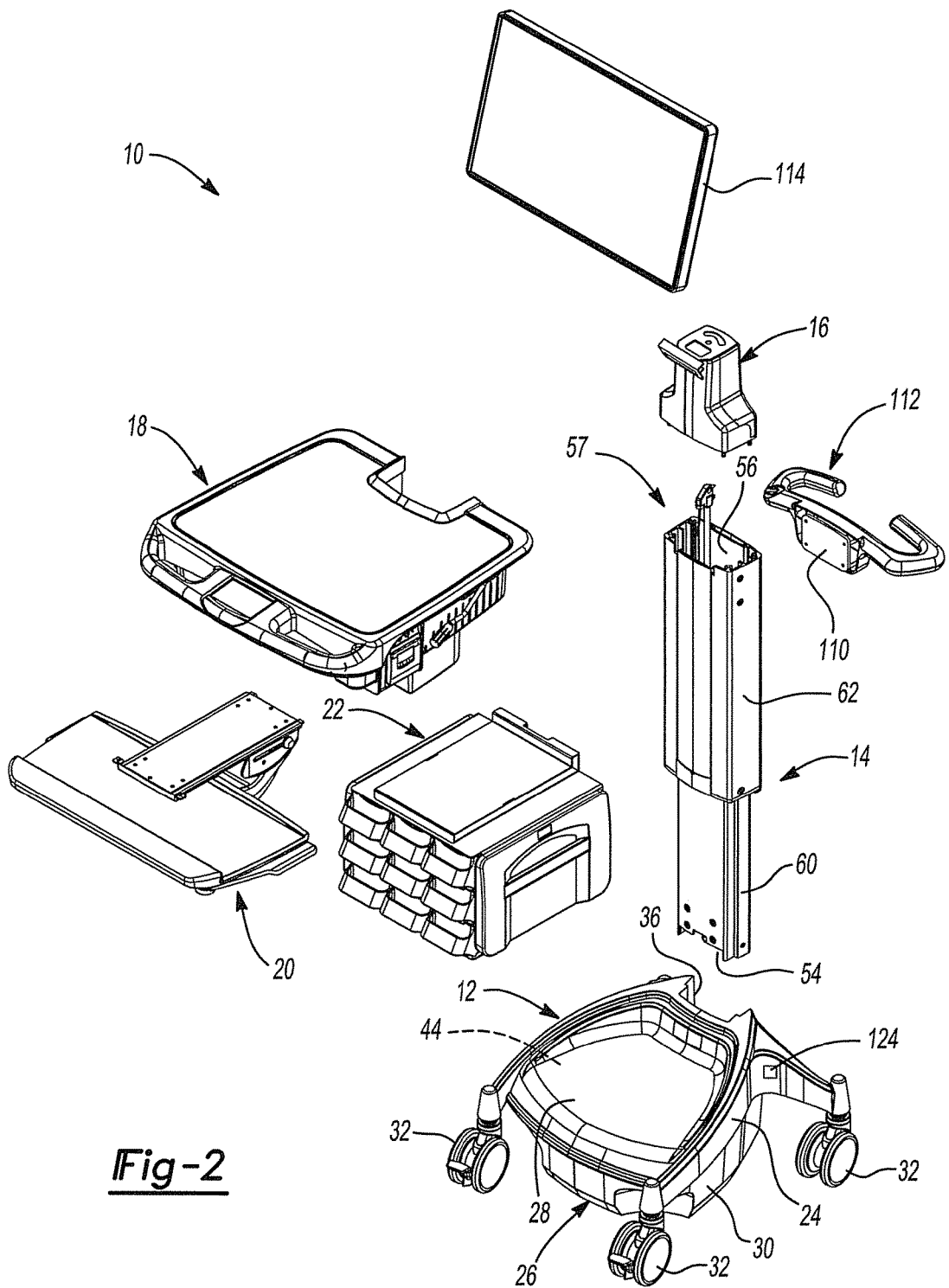
FIG. 2 is an exploded perspective view of the mobile computer workstation of FIG. 1.

A mobile computer workstation ("workstation") 10 according to the present disclosure can be applied to a variety of applications in a variety of health care, commercial, and industrial settings, as well as other work environments. As shown in FIGS. 1 and 2, the workstation 10 may include a base assembly 12, an adjustable column assembly 14, a monitor support assembly 16, a tray assembly 18, a keyboard tray assembly 20 and a storage module 22. Work settings in which the workstation 10 can be utilized include, but are not limited to, inventory control applications, maintenance applications, diagnostic applications, food service applications, quality control applications where, for instance, sampling and/or statistical analyses can take place, loading dock shipping and receiving applications, manufacturing assembly/parts tracking applications, pharmaceutical manufacturing and/or dispensing applications, or portable point-of-sale location applications. One type of workstation that is contemplated is a point-of-care ("POC") workstation, which can be specifically adapted for use in a medical facility, such as a hospital.

In a workstation equipped with an on-board computer, real time information exchange at a point-of-care can be accomplished. In such applications, selections, decisions, corrections, detections and data entry are all possible with the workstation of the invention.

When the workstation is used to its fullest advantage, general areas such as safety, control, and authorization are improved or made more efficient. Because real time records are capable of being recorded, redundancy in data or tasks can be reduced. For instance, information can be immediately and accurately exchanged, or when work is performed, charges associated with such work can be immediately issued. To accomplish such real-time information exchange, the workstation, and more specifically, the on-board computer system, can communicate, for example, with a central computer or a local area network for the facility within which the workstation is utilized.

Such communications can be by wired or wireless communications means. Various wireless communications protocols can be incorporated into and used with the workstation and its on-board computer system. For instance, well-known wireless communications protocols including IEEE 802.11 and Bluetooth® can be used. Any peripherals associated with the communications, such as network adapters and routers, for example, can be located within the workstation or integral with the workstation's on-board computer.

Referring now to FIGS. 1-4, the base assembly 12 may include a chassis frame 24, a housing 26 having upper and lower covers 28, 30, and a plurality of casters or wheels 32, such as two front wheels and two rear wheels. As shown in FIGS. 5 and 7, the chassis frame 24 may define a main opening 34, a channel 36 and one or more passages 38 extending between the channel 36 and the main opening 34. In some configurations, an L-shaped bracket 40 may be attached to the chassis frame 24 that includes one or more openings 42 that define the passages 38. As shown in FIG. 1, the adjustable column assembly 14 may be received in the channel 36 and secured to the chassis frame 24 by fasteners, snap fit, press fit, welding and/or any other attachment method. The wheels 32 can be attached to an underside of the chassis frame 24. One or more of the wheels 32 can include additional features like a lock pedal and swiveling capability, which can be used in any combination to facilitate desired motion and maneuvering capabilities of the workstation 10.

The housing 26 may be attached to the chassis frame 24 at the main opening 34 such that the lower cover 30 extends downward from an underside of the chassis frame 24. The upper cover 28 may be attached to the chassis frame 24 and/or the lower cover 30. In this manner, the chassis frame 24 and the upper and lower covers 28, 30 cooperate to define a cavity 44. The cavity 44 may be in airflow communication with the channel 36 via the passages 38. The lower cover 30 may include one or more air-inlet passages 45 through which ambient air can be drawn into the cavity 44.

A power supply 46 can reside within the cavity 44 of the housing 26 and may include, for example, a power adapter and charger 48 and/or one or more rechargeable batteries 50. The power supply 46 provides a compact power supply to all on-board electrical components, such as but not limited to a computer, monitor, peripherals, the adjustable column assembly 14, tray controller, storage module (if equipped), lights, and/or indicators. In some configurations, the power supply 46 has a plurality of independently replaceable batteries. The power adapter and charger 48 efficiently charges the batteries while maximizing the useful life of the batteries. The power supply 46 is scalable (e.g., it can be expanded or contracted in size and power) by increasing or decreasing the number of batteries included in the power supply 46. If supplied with AC power, the power supply 46 charges the batteries 50 and can provide DC power to the workstation 10, the on-board computer and any peripherals notwithstanding the charge level or condition of its batteries. The power adapter and charger 48 and batteries 50 are supported on a power supply support bracket 52 that is mounted to the chassis frame 24. The bracket 52 may include vent openings 53 to facilitate air flow through the cavity 44.

The power supply 46 and method for its operation and use provides for numerous beneficial features and advantages. For instance, a battery gauge included in the tray controller, can provide a user-detectable output such as, for example, a series of light emitting diodes (LEDs) representing various stages of battery charge such as 100%, 80%, 60%, 40%, 20%, and CHECK BATTERY, for example. A CHECK BATTERY feature can provide a visual or audible indication to a user if a low-battery condition is detected with any of the batteries 50 and/or if a problem is detected with the batteries 50 or the power adapter and charger 48.

The power supply 46 generates heat during operation. The heat generated by the power supply 46 may be vented from the cavity 44 of the housing 26 through the passages 38 and up through first and second vertically extending channels 54, 56 of the adjustable column assembly 14. The air-inlet passages 45 in the lower cover 30 may allow air from outside of the workstation 10 to be drawn into the cavity 44 to facilitate air flow and heat venting from the cavity 44 to the channels 54, 56. Cords, cables and/or wires 57 can also be routed from the power supply 46 through the passages 38 and channels 54, 56 to various electrically powered devices of the workstation 10.

The adjustable column assembly 14 may include first and second columns 60, 62. The column assembly 14 is attached to the base assembly 12 and supports the monitor support assembly 16, the tray assembly 18, the keyboard tray assembly 20 and the storage module 22. The monitor support assembly 16 may be mounted to the upper end of the second column 62 and may support one or more monitors 114. The column assembly 14 is operable to raise and lower a height of the monitor support assembly 16, the tray assembly 18, the keyboard tray assembly 20 and the storage module 22 relative to the base assembly 12 to any of a plurality of positions according to any given user's preference.

The first column 60 may be received in the channel 36 of the chassis frame 24 of the base assembly 12 and fixed to the chassis frame 24, as shown in FIG. 1. The first column 60 includes the first channel 54 extending therethrough. The second column 62 includes the second channel 56 and telescopically receives the first column 60 in the second channel 56. The second column 62 may include first and second pairs of parallel guide rails (not shown) that extend inward into the second channel 56 and extend between upper and lower ends of the second column 62.

The second column 62 may receive a bracket 110 to which a handle assembly 112 may be attached to the workstation 10. A lift mechanism (not shown) adjusts the vertical length of the column assembly 14 (i.e., a vertical position of the second column 62 relative to the first column 60) to establish and control the vertical positioning of the monitor support assembly 16, tray assembly 18, keyboard tray assembly 20, storage module 22 and handle assembly 112, as desired by the user.

Such adjustment can be accomplished by the user under power supplied by power supply 46 of the workstation 10. The lift mechanism can include a motorized, hydraulically, or pneumatically driven device, for example. The device can incorporate a gear mechanism, a ball screw mechanism, a spring, a piston, a cable, a spool, a pulley and similar types of structures or components. Alternatively, the lift mechanism can include a balancer device that enables the user to adjust the position of the second column 62 under force supplied by the user.

While the workstation 10 is applicable in a variety of professional and industrial settings, the advantages are easily describe in the context of a POC workstation configured for a medical environment. For instance, a nurse or other medical professional of a hospital staff may require access to patient information on a real-time basis at the point of application of medical care, such as with a patient while a medical professional makes rounds.

Figure 3:
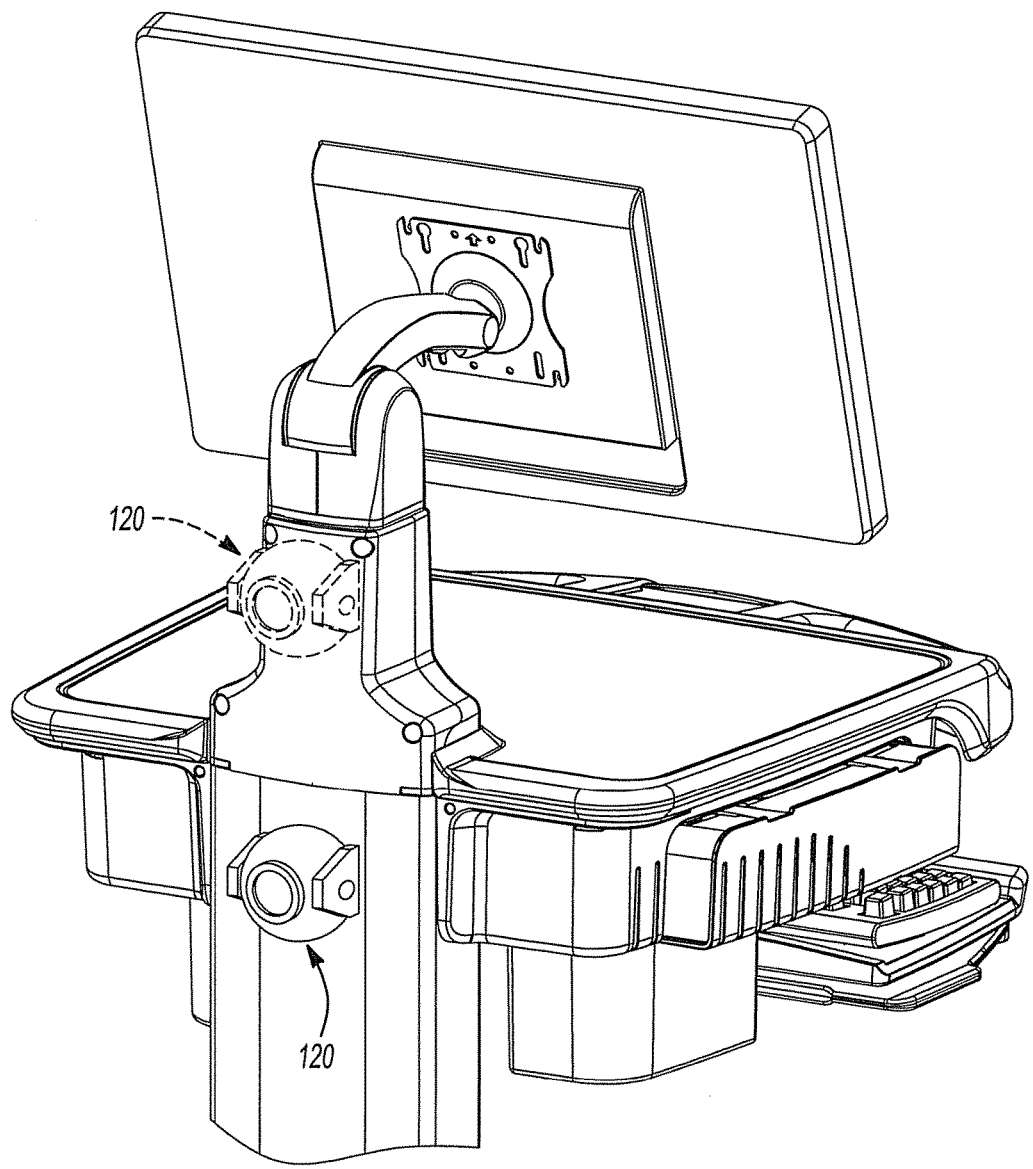
FIG. 3 is a perspective rear view of the mobile computer workstation of FIG. 1 in the direction of Arrow 3 (with the monitor removed)
Figure 4:
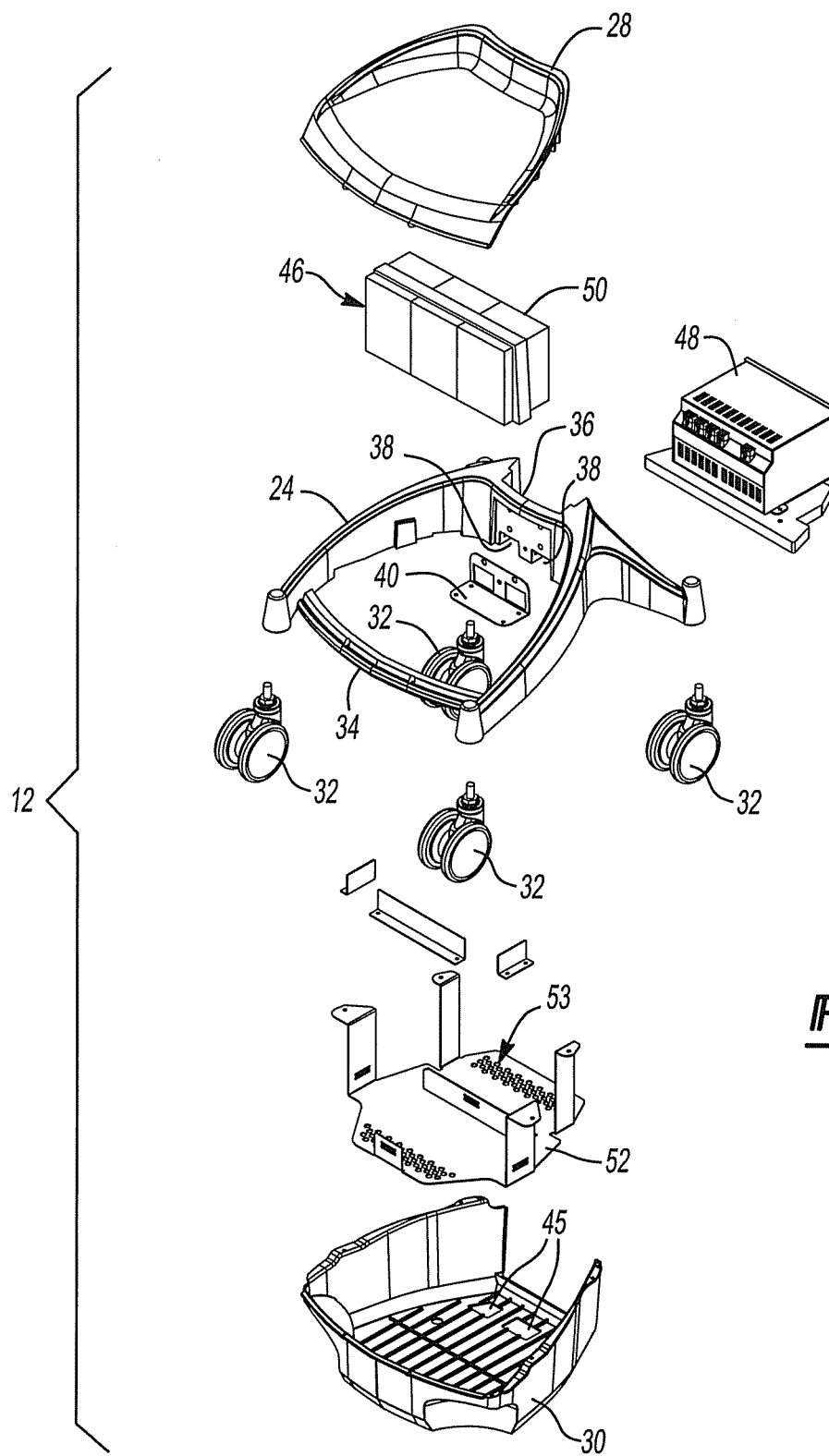
FIG. 4 is an exploded perspective view of a base assembly of the mobile computer workstation of FIG. 1.

A medical practitioner making the rounds may push the workstation 10 from room-to-room and use the same mobile workstation when attending to different patients. In some embodiments, the workstation 10 includes a navigation camera 120 as illustrated in FIG. 3. The power supply 46 provides electrical power (e.g., DC power) to the navigation camera 120 if that device does not incorporate its own internal power supply, such as a battery, for example.

The camera 120 aids the user in navigating and/or maneuvering the workstation 10 while pushing the workstation 10 from one location to another. As shown in FIG. 3, the navigation camera 120 is mounted to the workstation 10 in a rearward-facing manner such that its line of sight and field of view are directed from a location originating from the back of the workstation 10 (e.g., on the side of the workstation 10 that is generally opposite to the side that is occupied by the user during routine use of the workstation 10). As illustrated in FIG. 3, the navigation camera 120 may be mounted to the second column 62, the monitor support assembly 16, directly to the monitor 114, or in any other suitable location on the workstation 10. When the navigation camera 120 is operating, the monitor 114 can display an image of what is present behind the workstation 10, the user's view of which may otherwise be obstructed. Consequently, the user of the workstation 10 is able to "see" through the monitor 114 and/or workstation 10 to what may be on the other side of the workstation 10. As such, the monitor 114 of the workstation 10 becomes virtually "invisible" to the user and the user can more easily navigate and/or maneuver the workstation 10.

The navigation camera 120 can comprise an analog or digital camera device that captures image data and produces a video signal. The video signal can be received, for example, by the on-board computer of the workstation 10 and then routed to the monitor 114 for display. In such a configuration, the navigation camera 120 is a video device peripheral to the computer and connects to the computer in a well-known manner, such as by a USB connection. Alternatively, the navigation camera 120 video signal can be connected directly to a video input of the monitor 114, such as an analog or digital video input, bypassing the on-board computer of the workstation 10. The input to the monitor 114 can then be manually or automatically toggled between a video signal received from the computer and the video signal from the navigation camera 120. In either configuration, the wire(s), cord(s) and/or cable(s) associated with the navigation camera 120, computer and/or monitor 114 can be routed as previously described.

In some embodiments, the video signal from the navigation camera 120 can be displayed on the monitor 114 to occupy the entirety of the display of the monitor 114, or the video signal can appear in a window in the display of the monitor 114 having a size smaller than the size of the entirety of the display.

In yet another embodiment, as shown in FIGS. 1 and 2, a motion sensor 124 may be incorporated into the workstation 10. The motion sensor 124 may be incorporated into the base assembly 12, as shown in FIGS. 1 and 2. While the motion sensor 124 is depicted as being generally incorporated into the base assembly 12, it is understood that the motion sensor 124 may be incorporated into any component of the workstation 10. Further, while only one motion sensor is described, it is understood that a plurality of motion sensors may be incorporated within the workstation 10.

The motion sensor 124 is configured to sense a motion of the workstation 10. In some embodiments, the motion sensor 124 may communicate a motion signal to the on-board computer of the workstation 10. The motion signal may include a value that indicates at least one motion characteristic of the workstation 10. For example only, the motion characteristic may include an acceleration, a velocity, and/or a direction of a motion, and/or a duration of time over which the motion is sensed, or any other suitable characteristic of motion.

The on-board computer is configured to receive the motion signal and determine whether the motion of the workstation 10 is above a motion threshold. For example only, the on-board computer executes a motion detection application. The motion detection application is in communication with the navigation camera 120 via the on-board computer as described above. The motion detection application is configured to determine whether to initiate the navigation camera 120 in response to the motion signal. The motion detection application receives the motion signal and compares the value indicated by the motion signal with the motion threshold. By way of non-limiting example only, the value indicates a duration of the motion of the workstation 10. The motion threshold is a predetermined motion duration. The motion detection application determines whether the duration is above the predetermined motion duration.

When the duration is above the predetermined motion duration, the motion detection application initiates the navigation camera 120. The navigation camera 120 begins communicating a video signal to the on-board computer. The on-board computer displays the video signal on the monitor 114 as described above.

In other words, the motion detection application is configured to determine whether the workstation 10 is moving in a manner that indicates the user is pushing the workstation 10 from one location to another. When the motion detection application determines the workstation 10 is moving in this manner, the motion detection application utilizes the navigation camera 120 in order to allow the user to safely travel with the workstation 10 as described above. In some embodiments, the motion detection application may determine whether to initiate the navigation camera 120 in response to a motion direction of the workstation 10, a motion acceleration or speed of the workstation 10, or any suitable motion characteristic or combination of characteristics such as described above.

In another embodiment, the motion sensor 124 is in direct communication with the navigation camera 120. When the motion sensor 124 senses a motion of the workstation 10 that is consistent with moving the workstation 10 from location to location, the workstation 10 will automatically display the image from the navigation camera 120 on the monitor 114. For example only, the motion sensor 124 is configured to generate a motion signal when the motion sensor 124 determines a sensed motion is above a threshold. For example only, the motion sensor 124 compares a sensed motion to the threshold. When the sensed motion is above the threshold, the motion sensor 124 generates the motion signal. As described above, the sensed motion may include an acceleration, speed, direction, duration, or any other suitable motion characteristics. The motion sensor 124 communicates the motion signal to the navigation camera 120.

The navigation camera 120 is configured to communicate a video signal in response to receiving the motion signal. As described above, the navigation camera 120 may be in direct communication with the monitor 114. The navigation camera 120 communicates the video signal to the monitor 114. The monitor 114 automatically displays the video signal. In another embodiment, the navigation camera 120 is in communication with the on-board computer of the workstation 10. The on-board computer receives the video signal and communicates the video signal to the monitor 114. The monitor 114 displays the video signal. In this manner, the workstation 10 may automatically begin displaying a video signal captured by the navigation camera 120 when the user moves the workstation 10 from location to location.

In some embodiments, the workstation 10 automatically stops displaying the video signal from the navigation camera 120 in response to the workstation 10 not moving. For example only, as described above, the navigation camera 120 receives the motion signal indicating the workstation 10 is moving from location to location. The motion sensor 124 continuously communicates the motion signal when the motion sensor 124 determines the workstation 10 is moving (as described above). When the motion sensor 124 determines the workstation 10 is no longer moving, the motion sensor 124 discontinues communicating the motion signal. For example, the motion sensor 124 compares a currently sensed motion of the workstation 10 to a second threshold. The currently sensed motion may be a deceleration, speed or a duration of non-movement, for example. The second threshold may be a value predetermined to indicate the workstation 10 is not moving. For example, the second threshold may be a low speed or a duration of non-movement. In one example, the motion sensor 124 determines the workstation 10 is no longer moving when the currently sensed motion is a duration of non-movement of the workstation 10. When the duration of non-movement is above the second threshold, the motion sensor 124 discontinues generating the motion signal.

When the navigation camera 120 discontinues receiving the motion signal, the navigation camera 120 discontinues communicating a video signal to monitor 114. The monitor 114 discontinues displaying the video signal. The workstation 10 resumes a normal operating mode. In another example, the navigation camera 120 discontinues communicating the video signal to the on-board computer. The on-board computer discontinues displaying the video signal on the monitor 114. The workstation resumes operating in the normal mode. As described above, the motion sensor 124 may communicate the motion signal to the on-board computer. When the motion sensor 124 communicates the motion signal to the on-board computer, the motion detection application determines whether to instruct the navigation camera 120 to discontinue communicating a video signal.

As described above, the motion detection application is configured to determine whether the workstation 10 is moving. The motion detection application receives the motion signal and compares the value indicated by the motion signal with the motion threshold. By way of non-limiting example only, the value indicates a duration of the motion of the workstation 10. The motion threshold is a predetermined motion duration. The motion detection application determines whether the duration is below the predetermined motion duration. When the duration is below the predetermined motion duration, the motion detection application instructs the navigation camera 120 to discontinue communicating a video signal. In this manner, the motion detection application returns the workstation 10 to the normal operating mode. It is understood that the normal operating mode may include any operating mode consistent with the description of the workstation 10 described above.

In yet another embodiment, the workstation 10 is configured to deactivate the navigation camera 120. The workstation 10 may discontinue displaying a video signal from the navigation camera 120 in response to receiving an input from the user. In one example, the monitor 114 displays the video signal from the navigation camera 120 according the any of the embodiments described above. Once the monitor 114 begins displaying the video signal from the navigation camera 120, the monitor 114 continuously displays the video signal from the navigation camera 120 regardless of whether or not the workstation 10 is moving.

In this manner, when the user stops pushing the workstation 10, the display does not resume operating in a normal mode. This may be advantageous in order to maintain confidentiality of patient information. For example only, a nurse may push the workstation 10 from one room to another room. Prior to utilizing the workstation 10 for the purposes of patient care, the nurse may leave the workstation 10 unattended. While the workstation 10 is unattended, the monitor 114 continues to display the video signal from the navigation camera 120, thus protecting any patient information that may be accessible from the workstation 10.

In order to resume operating in a normal mode, the workstation 10 may require a user verification. In one embodiment, the workstation 10 may include an identification card scanner. The user may swipe an identification card in the identification card scanner. In another example, the identification card scanner may include a proximity sensor. The proximity sensor is configured to determine when a valid identification card is within a predetermined proximity to the workstation 10. The identification card scanner validates the identification card. The identification card scanner communicates a verification signal to the on-board computer. The on-board computer is configured to discontinue displaying the video signal on the monitor 114 and resume operating in a normal mode in response to receiving the verification signal.

In yet another example, the on-board computer may receive a user input from one of a keyboard or mouse connected to the on-board computer. Upon receiving the input from the keyboard of mouse, the on-board computer displays a dialog box on the monitor 114. The dialog box may request the user to input a user name and password. The on-board computer validates the user name and password. The on-board computer resumes operating in a normal mode in response to receiving a valid user name and password.

As illustrated in FIGS. 3 and 5, the navigation camera 120 can be located on or mounted to the second column 62. It is understood that the navigation camera 120 may also be located on or mounted to the monitor or to the monitor support structure of the workstation 10. The navigation camera 120 is located on the workstation 10 so that the navigation camera 120 has a clear line of sight and field of view in the rearward direction from the workstation 10 that is not obstructed by the workstation 10 or its components, notwithstanding the vertical position of the work surface or adjustable components of the workstation 10.

With reference to FIG. 6, yet another alternative embodiment of the workstation 10, a camera 220 may be incorporated into the workstation 10 that can be used both as a navigation camera as well as a video conferencing camera. In one embodiment, the workstation 10 includes a videoconferencing application. The videoconferencing application provides the ability for a user to interact remotely with others while simultaneously reviewing a patient's information, like a medical chart or diagnostic information. Specifically, remote experts can be consulted and provide advice with easy access to up to date patient information and vital statistics.

In some embodiments, the workstation 10 including the videoconferencing application may include a monitor having an extra-large display, or it may include dual monitors. The dual monitors allow the use of two high-resolution imaging displays. As such, diagnostic images, electronic medical records (EMR), or other patient data may be shared. The camera 220 is also incorporated to permit two-way video conferencing.

The camera 220 can be mounted to the workstation 10 via a camera mount 128. The camera mount 128 may be a rigid column configured to place the camera 220 at or near an edge of the monitor 114. For example, as shown in FIG. 6, the camera mount 128 may place the camera 220 at or above a top edge of the monitor 114. It is understood that while only placing the camera 220 at or above the top edge of the monitor 114 is described, the camera 220 may be placed at or near a first side of the monitor 114, at or near a second side of the monitor 114, or at or below at bottom edge of the monitor 114. The camera mount 128 may be coupled to the second column 62 or to the monitor support structure of the workstation 10 via a mounting bracket 132. In some embodiments, the camera mount 128 may be extensible or otherwise vertically adjustable, such that the user may raise or lower the camera 220 according to a user's preference.

The camera 220 may be mounted on a swivel 136, such that the camera 220 can be rotated and positioned in a forward-facing (i.e., facing the user) direction where it can serve as the camera for the videoconferencing application, and in a rearward-facing direction where it can serve as a navigation aid to the user when moving the workstation 10 as described above.

The position of the camera 220 can be controlled and manipulated manually by the user, or the camera 220 can be positioned automatically. For example, the camera 220 may be normally located in a first, rearward-facing position where it serves as a navigation aid to the workstation 10 user as described above. In the first position, the camera 220 can be activated in any manner described above. The user may then manually turn the camera 220 on the swivel 136 in order to place the camera in a second position. When the camera 220 is in the second position, the user may start the videoconferencing application and utilize the camera 220. Alternatively, upon initiation of the videoconferencing application, the camera 220 automatically repositions to the second, forward-facing position where it serves as the camera for the videoconferencing application.

For example, the videoconferencing application may communicate a signal to the camera 220 indicating the videoconferencing application has been initiated. The swivel 136 may include a solenoid or an electric motor, for example. Upon receiving the signal from the videoconferencing application, the solenoid or motor automatically rotates the swivel 136 in order to place the camera 220 in the second position. Conversely, when the videoconferencing application is closed by the user, the on-board computer communicates a signal to the camera 220 indicating the videoconferencing application is closed. The solenoid or motor, in response to receiving the signal, automatically rotates the swivel 136 in order to place the camera 220 in the first position. Additionally or alternatively, the camera 220 automatically rotates to the first position in response to the workstation 10 moving. For example, camera 220 is utilized as a navigation camera when the workstation 10 is determined to be moving according to any of the embodiments described above. The camera 220 receives a motion signal indicating the workstation 10 is moving.

The motor rotates the swivel 136 in order to place the camera 220 in the first position. It is understood that the workstation 10 may be configured to override the video conferencing application in order to allow the camera 220 to be utilized as a navigation camera. Further, the workstation 10 may be configured to request input from the user to determine whether to override the videoconferencing application. For example, when the workstation 10 is determined to be moving, the on-board computer may display a dialog box on the monitor 114. The dialog box may request the user indicate whether to override the videoconferencing application.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A mobile computer workstation comprising:
a base assembly including a plurality of wheels;
an adjustable column assembly mounted to the base assembly and adapted to support a computer monitor;
a camera configured to communicate a video signal, the camera being mounted on the workstation such that a line of sight of the camera is directed rearward from the computer monitor;
a computing device stored within the workstation operatively coupled to the camera and the computer monitor, the computing device configured to:
determine whether the workstation is moving based on a comparison of a sensed motion of the workstation and a predetermined motion threshold; and
in response to the comparison:
initiate the camera;
receive the video signal from the camera; and
display the video signal on the computer monitor.

2. The system of claim 1 further comprising a motion sensor configured to sense a first sensed motion of the workstation.

3. The system of claim 2 wherein the motion sensor communicates the first sensed motion to the computing device.

4. The system of claim 3 wherein the computing device, in response to the first sensed motion being greater than the motion threshold, initiates the camera and displays the video signal on the computer monitor.

5. The system of claim 4 wherein the motion sensor communicates a second sensed motion of the workstation.

6. The system of claim 5 wherein the computing device, in response to the second sensed motion being less than the motion threshold, deactivates the camera and returns the workstation to a normal operating mode.

7. The system of claim 1 wherein the camera is mounted a camera mount extending from the workstation such that the camera mount places the camera in a position near an edge of the computer monitor.

8. The system of claim 7 wherein the camera is mounted on a swivel coupled to the camera mount and wherein the camera is rotatably movable between a first position and a second position.

9. The system of claim 8 wherein the camera is manually rotated by a user of the workstation between the first position and the second position.

10. The system of claim 8 wherein the camera is automatically rotated between the first position and the second position in response to a sensed motion of the workstation.

11. A method for displaying a video image on a computer monitor of a mobile computer workstation comprising:
comparing a sensed motion of the workstation and a predetermined motion threshold,
determining, in response to the comparison, whether the workstation is moving;
initiating, in response to the determination, a camera configured to communicate a video signal, the camera being mounted on the workstation such that a line of sight of the camera is directed rearward from the computer monitor;
receiving, in response to initiating the camera, the video signal; and
displaying the video signal on the computer monitor.

12. The method of claim 11 further comprising sensing a first sensed motion of the workstation.

13. The method of claim 12 further comprising receiving the first sensed motion.

14. The method of claim 13 further comprising initiating the camera and displaying the video signal on the computer monitor in response to the first sensed motion being greater than the motion threshold.

15. The method of claim 14 further comprising receiving a second sensed motion of the workstation.

16. The method of claim 15 further comprising deactivating the camera and returning the workstation to a normal operating mode in response to the second sensed motion being less than the motion threshold.

17. The method of claim 11 further comprising mounting the camera on a camera mount extending from the workstation such that the camera mount places the camera in a position near an edge of the computer monitor.

18. The method of claim 17 further comprising mounting the camera a swivel coupled to the camera mount and wherein the camera is rotatably movable between a first position and a second position.

19. The method of claim 18 further comprising manually rotating, by a user of the workstation, the camera between the first position and the second position.

20. The method of claim 18 further comprising automatically rotating, the camera between the first position and the second position in response to a sensed motion of the workstation.

* * * * *

UNITED STATES PATENT AND TRADEMARK OFFICE
CERTIFICATE OF CORRECTION

| | | |
|---|---|---|
| PATENT NO. | : 9,973,736 B2 | Page 1 of 1 |
| APPLICATION NO. | : 14/768616 | |
| DATED | : May 15, 2018 | |
| INVENTOR(S) | : Roberts et al. | |

It is certified that error appears in the above-identified patent and that said Letters Patent is hereby corrected as shown below:

In the Claims

Column 12, Line 8, Claim 11, insert after workstation -- including a base assembly having a plurality of wheels, the method --

Column 12, Line 10, Claim 11, delete "threshold," and insert -- threshold; --

Column 12, Line 12, Claim 11, insert after workstation -- including the base assembly --

Signed and Sealed this
Twenty-fourth Day of July, 2018

Andrei Iancu
*Director of the United States Patent and Trademark Office*